US006433690B2

(12) United States Patent
Petelenz et al.

(10) Patent No.: US 6,433,690 B2
(45) Date of Patent: Aug. 13, 2002

(54) ELDERLY FALL MONITORING METHOD AND DEVICE

(75) Inventors: Tomasz J. Petelenz; Stephen C. Peterson; Steven C. Jacobsen, all of Salt Lake City, UT (US)

(73) Assignee: Sarcos, L.C., Salt Lake City, UT (US)

( * ) Notice: Subject to any disclaimer, the term of this patent is extended or adjusted under 35 U.S.C. 154(b) by 0 days.

(21) Appl. No.: 09/734,099

(22) Filed: Dec. 11, 2000

Related U.S. Application Data

(63) Continuation-in-part of application No. 09/179,668, filed on Oct. 27, 1998, now Pat. No. 6,160,478.

(51) Int. Cl.[7] .............................................. G08B 23/00
(52) U.S. Cl. ............................... 340/573.1; 340/573.7; 340/689
(58) Field of Search ................................ 340/506, 539, 340/573.1, 573.4, 689, 573.7, 576, 686.1; 128/903, 904; 600/300

(56) References Cited

U.S. PATENT DOCUMENTS

| | | | | |
|---|---|---|---|---|
| 4,110,741 A | * | 8/1978 | Hubert et al. ............. 340/573.1 |
| 4,295,133 A | | 10/1981 | Vance ...................... 340/573.4 |
| 4,858,622 A | | 8/1989 | Osterweil ................ 340/573.1 |
| 5,012,411 A | | 4/1991 | Policastro et al. .......... 600/485 |
| 5,235,319 A | | 8/1993 | Hill et al. ................. 340/573.4 |
| 5,515,858 A | | 5/1996 | Myllymaki ................ 600/301 |
| 5,519,380 A | | 5/1996 | Edwards .................. 340/573.4 |
| 5,544,649 A | | 8/1996 | David et al. ............... 600/301 |
| 5,544,661 A | | 8/1996 | Davis et al. ................ 600/513 |
| 5,564,429 A | | 10/1996 | Bornn et al. ................ 600/508 |
| 5,722,999 A | | 3/1998 | Snell ........................... 607/32 |
| 5,752,976 A | | 5/1998 | Duffin et al. ................. 607/32 |
| 5,790,981 A | | 8/1998 | Bzoch ............................ 2/22 |
| 5,844,488 A | | 12/1998 | Musick .................... 340/573.4 |
| 5,918,310 A | | 7/1999 | Farahany ......................... 2/23 |
| 5,940,004 A | * | 8/1999 | Fulton ........................ 340/539 |
| 6,201,476 B1 | * | 3/2001 | Depeursinge et al. .... 340/573.1 |
| 6,208,251 B1 | * | 3/2001 | Cadet et al. ............. 340/573.1 |

OTHER PUBLICATIONS

"Companion," Pioneer Medical Systems, Inc., 37 Washington St., Melrose, MA 02176, 1999.
"1–800–Med–Alert, Personal Response Services".
"LifeGuard Personal Emergency Response System," Lifegard of America, Inc.
"Lifeline Personal Response and Support Services," Lifeline Systems, Inc., 111 Lawrence St., Framingham, MA 01702–8156, 1999.

* cited by examiner

*Primary Examiner*—Van T. Trieu
(74) *Attorney, Agent, or Firm*—Thorpe North & Western, LLP

(57) ABSTRACT

A method and system for recording acceleration and body position data from elderly or disabled persons. The fall monitoring system includes signal feature extraction and interpretive methods for characterizing accelerations and body positions during fall events. The system can detect health and life threatening fall events in elderly persons, and can autonomously notify nursing personnel or family members that the person is in need of immediate assistance.

23 Claims, 7 Drawing Sheets

ELDERLY FALL MONITORING METHOD AND DEVICE

This application is a continuation-in-part of U.S. patent application Ser. No. 09/179,668 filed on Oct. 27, 1998, now issued as U.S. Pat. No. 6,160,478.

TECHNICAL FIELD

This invention relates generally to the field of motion monitors for patients, and more particularly to an improved monitor for bio-mechanically characterizing falls in patients and providing an alarm in case of a fall.

BACKGROUND ART

Our aging population, improved health care, and an increasing number of working women create a demand for technologies allowing older persons to live independent lives. This number, in the U.S. alone, is estimated at 27 million people and will grow to 50 million by the year 2010. Thus, there are significant needs in the development of assistive technologies that allow older people to live alone safely.

Health-threatening falls are an important epidemiological problem in a growing segment of the aging population. Studies indicate that approximately two thirds of accidents in people 65 years of age or older, and a large percentage of deaths from injuries are due to falls. It has been estimated that approximately 1.6 million hip fracture injuries worldwide in 1990 were due to falls, and that this number will increase 6.26% by 2050, with the highest incidences recorded in Northern Europe and North America. In the elderly, 90% of hip fractures happen at age 70 and older, and 90% are due to falls. The falls are usually due (80%) to pathological balance and gait disorders and not to overwhelming external force (i.e., being pushed over by some force). More than 50% of elderly persons suffer from arthritis and/or orthopedic impairments, which frequently leads to falls. Specifically prone to falls are women experiencing a higher percentage of arthritis-related structural bone changes. It is estimated that approximately 5% of falls result in fracture and 1% of all falls are hip fractures. The percentages vary slightly in different geographical regions (e.g., Japan, Scandinavia), but the consensus of the available research is that the falls are a significant epidemiological problem in the growing elderly population.

Among older people in the U.S. (age 65+) there are approximately 750,000 falls per year requiring hospitalization due to either bone fracturing (approx. 480,000 cases) or hip fracturing (approx. 270,000 cases). The result of such injuries is an average hospital stay between 2 and 8 days. Assuming the average cost of $1,000 per hospital day, a total cost of falls in the elderly for the health care industry can be estimated at three billion dollars per year. This figure is likely to increase as the older aged segment of the population increases.

Falls in elderly people have been recognized as a major health problem in an aging population. Physical activity patterns, detecting the occurrence of falls, and recognizing body motion patterns inevitably leading to falls are not well understood due to the lack of systems which allow continuous monitoring of patients in an accurate, convenient, unobtrusive and socially acceptable manner.

SUMMARY OF THE INVENTION

This invention provides a method for monitoring a person's fall using an accelerometer included in a personal monitoring device configured to be carried on the person. The monitoring device has a microprocessor and a memory buffer, and data is stored in the buffer of the personal monitoring device. The first step in the method is sampling an output from the accelerometer indicative of body acceleration and body angle. The next step is detecting whether the body angle is in a steady state indicative of a fall for at least two seconds. Then the fall duration is measured by reading back through the buffer. Another step is determining if an uncontrolled fall has taken place by testing whether the fall duration is less than a time threshold. The last step is determining whether a severe fall has occurred by comparing an angular rate of change of the body angle and an acceleration amplitude change to a severity threshold.

In accordance with another aspect of the present invention, the method monitors a person's fall using a single-dimensional accelerometer in a monitoring device on the person. The method includes the step of detecting whether the person's acceleration exceeds a maximum threshold. The next step is collecting at least 2 seconds of additional acceleration data in a buffer. Another step is finding a largest acceleration sample value in the buffer. The final step is signaling that a fall has taken place when that acceleration sample value exceeds a predetermined maximum threshold.

Additional features and advantages of the invention will be set forth in the detailed description which follows, taken in conjunction with the accompanying drawings, which together illustrate by way of example, the features of the invention.

DETAILED DESCRIPTION

Figure 1:
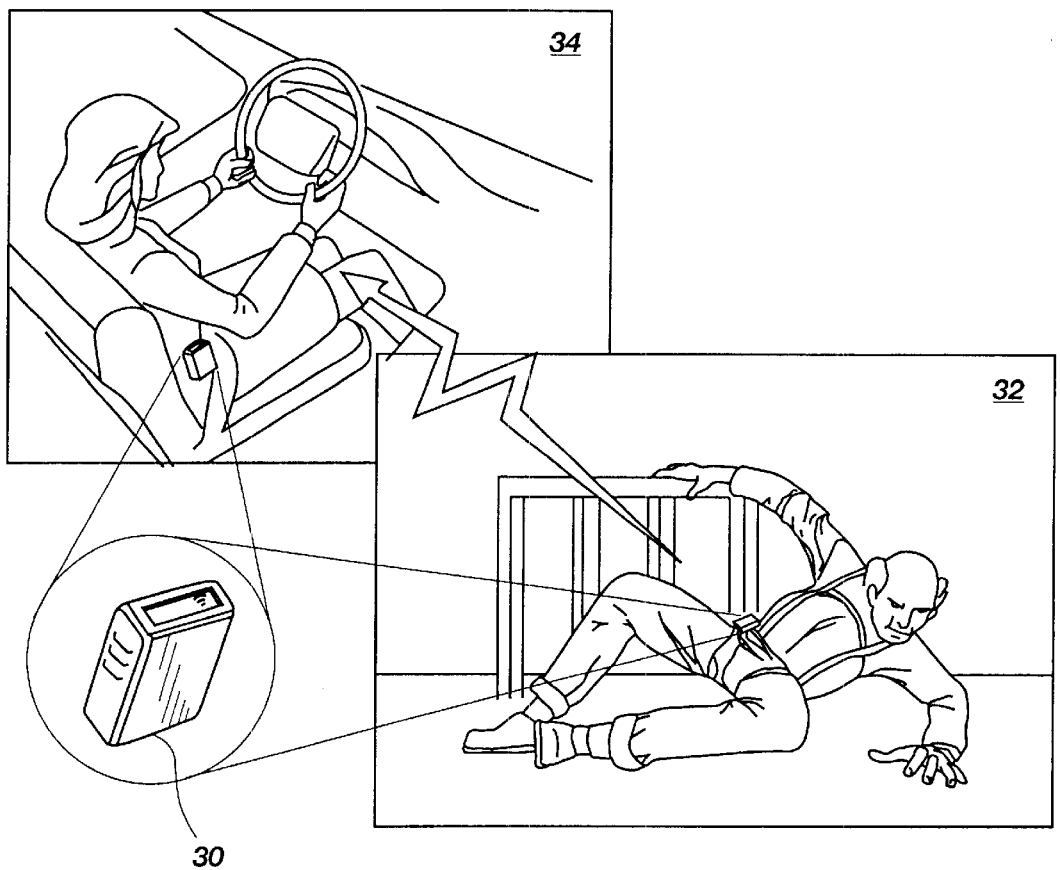
FIG. 1 illustrates a fall detection device which provides fall information to a caregiver.

For the purposes of promoting an understanding of the principles of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

The method and system of the present invention allows for remote monitoring of health-threatening fall events in nursing home patients or in similar care facilities. It detects serious fall events and provides rapid notification of emergency help for elderly or disabled persons who live alone. In addition, the physical movements of an elderly person can be monitored to evaluate their overall physical activity.

FIG. 1 illustrates a monitor 30 which is pager-sized or smaller for physical activity monitoring. The size of the invention enables a patient 32 or person to wear the device continually, thus providing an added measure of security for the elderly or homebound. A continuously wearable device also increases the "peace of mind" for their working children, nurses and/or caretakers 34, who are not within immediate reach of the elderly person or patient. The system is small, lightweight, ergonomic, unobtrusive, and operates autonomously. In addition, the device is self-contained and does not require wiring, installation, calibrations or programming that may be inconvenient or overly difficult for elderly persons to perform.

Figure 2:
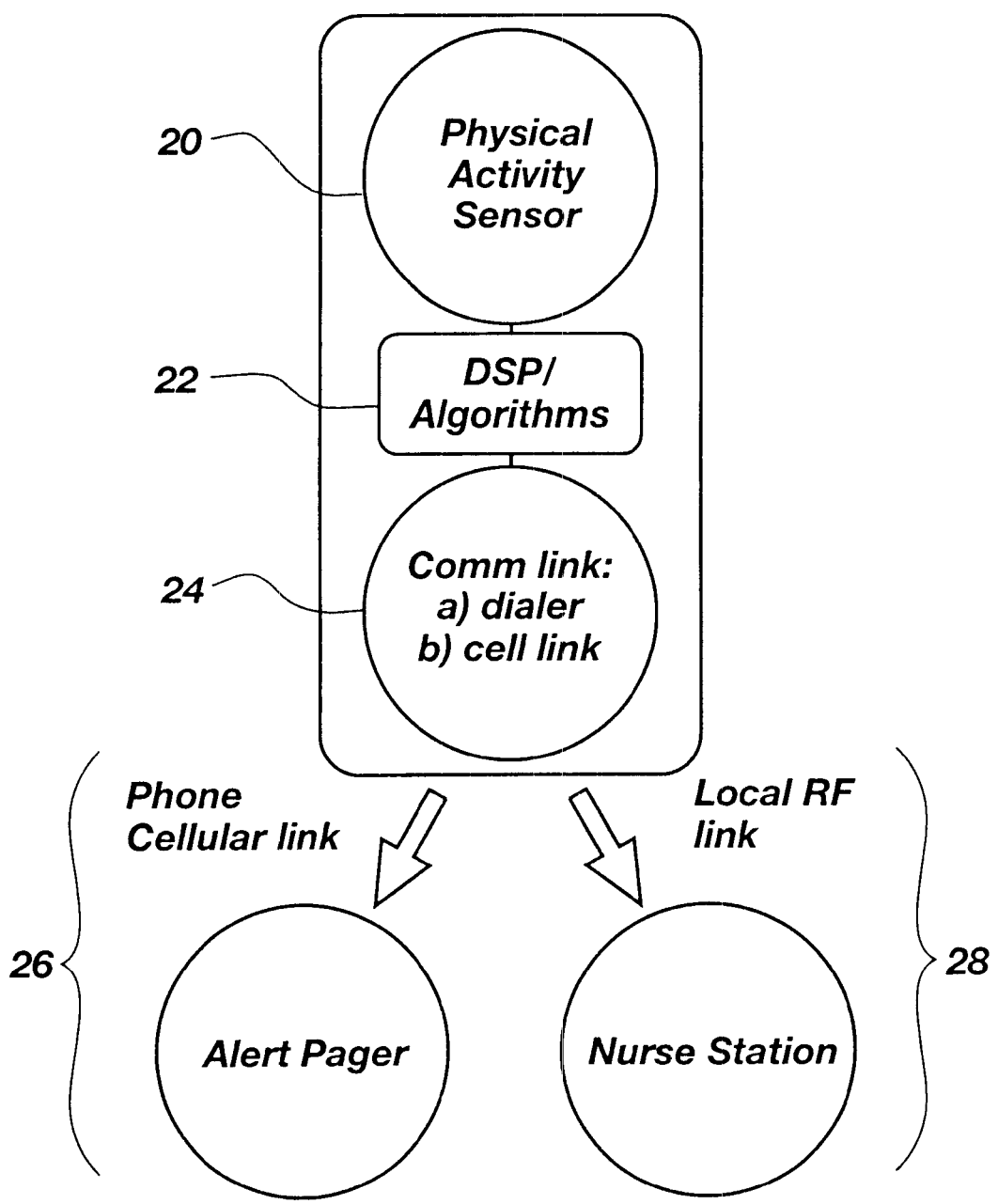
FIG. 2 is a block diagram of a fall detection device and the associated communications networks.

Referring now to FIG. 2, an important characteristic of the present invention is that acceleration and body position sensors 20 in the monitor provide information for detecting or predicting a fall. This is performed using a software method 22 or digital signal processing (DSP) which recognizes body movement and position patterns that indicate a fall has occurred or could occur. When fall patterns are detected, a fall warning can be transmitted to a careprovider via a communications link 24. It is also possible to produce a preliminary fall warning to an elderly patient who is wearing the device so they will be encouraged to lay or sit down.

The monitor device communicates with a pager monitor or station using conventional RF (radio frequencies) 28 or automated telephone dialer technology. A signal transmitted to the pager monitor or station is then transferred to an operator or attendant who can dispatch emergency care or treatment. The monitor device may also be connected to a cellular data modem 26 for transmitting an alert signal to a commercial paging network. A wireless communication link allows the patient to be monitored regardless of their location. When the monitoring device is connected to a cellular or another communications network, a patient can be monitored while they are outside, traveling, or shopping.

This system uses an effective method for detecting the fall of elderly people using accelerometers attached at the waist. The inventors of this invention believe that the lack of the significant prior work using accelerometers to detect falls is due to the lack of an effective computational method. This device includes at least two robust methods that can distinguish between the falls and non-falls.

The fall monitoring hardware includes at least one accelerometer unit which has one two-axis accelerometer. The two units are packaged in a configuration with one axis from each unit orthogonal to the other, while two other axes are arranged anti-parallel and orthogonal to the first two. In this way, the sensor system formed by the two accelerometers, measures three orthogonal accelerations. When the device is attached to the waist with a stiff belt (e.g., a leather belt) and the anti-parallel axes are more or less vertical.

In a preferred embodiment, the accelerometers have a G (gravity) range of +/−2 Gs and provide both a pulse width modulated (PWM) output or a voltage output that has a sensitivity of 300 mV/G. The PWM output is preferably used. The PWM output of the accelerometer is converted to gravity values by an onboard microcontroller. An important function of the software connected to the accelerometer is to set the sampling rate at a fixed interval. This function is accomplished using a microcontroller counter for precisely determining the time interval. In order to facilitate the data processing, it is important that the sampling period of the data acquisition be fixed. Such data acquisition is called true real time data acquisition.

Now the biomechanics of the present method and device will be discussed. The method must analyze the fall process, time duration, and impact amplitude. These issues are determining factors in distinguishing uncontrolled falls from controlled falls, such as lying down to rest.

In the steady state after a fall event, the user's body is defined to be horizontal. The accelerometer-based sensor is capable of measuring the gravity vector in the sensor coordinate system. If the sensor coordinate system moves with the user, the gravity vector may be used to indicate when the user is in the horizontal position or upright position.

Figure 3:
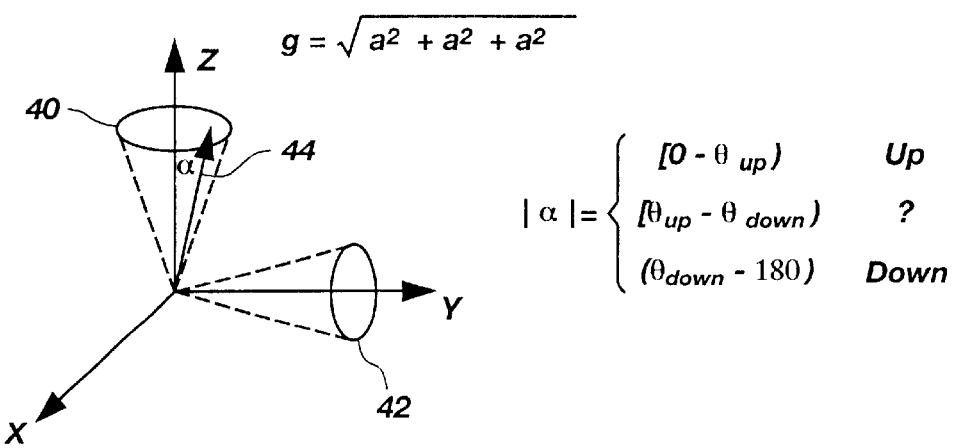
FIG. 3 represents a body position vector.

Since the gravity vector is static in the global coordinate system but changes orientation in our sensor coordinate system, two cones 40, 42 are considered in our sensor coordinate system as shown in FIG. 3. When the gravity vector is in the upper cone 40, the user is in the upright position. This system must measure the falling time and the length of time a person remains horizontal. Both uncontrolled falls and controlled falls consist of the change of the body orientation. Specifically, the body angle 44 changes from approximately vertical to horizontal. In the preferred embodiment of the invention, it is assumed that during the uncontrolled fall, and after the fall, the body remains in a horizontal orientation for at least two seconds. Such an assumption does not assume that the body cannot roll along a horizontal axis.

In the event of fall, the downward acceleration of the center of the mass is approximately less than or equal to g (gravity). The time it takes for the center of mass to reach the ground is governed by the equation $t=\sqrt{d/g}$, where d is the distance of travel and t is the time for the object to travel at the acceleration of g through the distance of d. Assuming that the average height of a person is about 6 feet and the center of mass in the vertical direction is 3.5 feet, the time it takes for the center of mass to reach the ground is approximately 0.335 seconds. The timing is important in determining the filtering cutoff frequency.

Since the initial downward velocity in the event of a fall is substantially zero, the velocity of the center of mass before reaching the ground (before the impact) is $v=g\cdot t$, where v is the velocity before the impact and t is the time that the center of mass traveled at the acceleration of g starting from zero initial velocity. The velocity from the above equation determines the minimum impact acceleration.

The present method assumes that there are two kinds of the falls: controlled and uncontrolled. A controlled fall is defined as a fall where the subject does not lose consciousness in the fall process, and actively tries to prevent the fall from happening. An uncontrolled fall is when the subject loses consciousness at some time during the fall process or is unable to prevent the fall from happening. Certain events, such as going to bed or sitting on a sofa, are not defined as a fall. These events typically consist of a two-event process (sit, then lie down).

The falling events are distinguished from the lying event by the two-event process. The uncontrolled falling event is distinguished from the controlled falling event by the time duration. An uncontrolled event will have a shorter time period than a controlled event.

Effectively, three components of acceleration are measured with an intrinsic sensor coordinate system or Cartesian coordinate system. The gravitational acceleration vector 46 is tracked in the sensor coordinate system, as shown in FIG.

4, for determining if the subject has fallen or not. It should be mentioned that the measurement of a gravitational vector is corrupted by the subject's body acceleration due to voluntary movements, but this can be taken into account. If the gravitational acceleration vector is lined up with the z-axis when the subject is standing up, the lying condition can be conveniently determined by examining the angle formed by the gravitational vector and the z-axis vector.

However, it is possible that the sensor unit might not be mounted perfectly on the subject's waist. The gravitational vector might not be lined up with the z-axis as shown in FIG. 3. In order to increase the accuracy of the fall detection method, the sensor coordinate system is rotated so that when the user's body is in the upright position and the gravity vector is aligned with a new z-axis. A coordinate rotation can be easily accomplished by conducting a calibration procedure when the user first puts on the sensor unit. The calibration creates another coordinate system called the corrected coordinate system, which is also fixed to the sensor system and rotated with respect to the intrinsic sensor coordinate system. The gravity vector is now lined up with its z-axis in the corrected coordinate system when the user is standing up. The Y-axis of the corrected coordinate system is determined by making it perpendicular to both the Z-axes of the intrinsic sensor coordinate system and the gravity vector. A direction is determined by using the right-hand rule, assuming the z-axis in the intrinsic sensor coordinate is rotated to the gravity vector. The X-axis of the corrected coordinate system is also determined by the right-hand rule based on the Z and Y-axes of the corrected coordinate system. The transformation of any vector from the corrected coordinate system to the sensor coordinate system can be established with two consecutive rotations: first, rotate about $Y_c$ by q, then rotate about Z by a. The rotation matrices are given below:

$$\begin{bmatrix} x \\ y \\ z \end{bmatrix} = \left( \begin{bmatrix} \cos\theta & -\sin\theta & 0 \\ \sin\theta & \cos\theta & 0 \\ 0 & 0 & 1 \end{bmatrix} \begin{bmatrix} \cos\alpha & 0 & \sin\alpha \\ 0 & 1 & 0 \\ -\sin\alpha & 0 & \cos\alpha \end{bmatrix} \right)^{-1} \begin{bmatrix} x \\ y \\ z \end{bmatrix}$$

The next expression is needed for computing the gravitational vector in the corrected coordinate system from the sensor intrinsic coordinate system in real time.

$$\begin{bmatrix} x \\ y \\ z \end{bmatrix} = \left( \begin{bmatrix} \cos\theta & -\sin\theta & 0 \\ \sin\theta & \cos\theta & 0 \\ 0 & 0 & 1 \end{bmatrix} \begin{bmatrix} \cos\alpha & 0 & \sin\alpha \\ 0 & 1 & 0 \\ -\sin\alpha & 0 & \cos\alpha \end{bmatrix} \right)^{-1} \begin{bmatrix} x \\ y \\ z \end{bmatrix}$$

Even though this step requires matrix multiplication and inversion, it only needs to be done once and does not need to be computed in real time.

The detailed steps required to detect the fall of an individual wearing the present device will now be discussed. The first step is detecting if the person's body has become substantially horizontal. If the fall event (controlled or uncontrolled) occurred, the person's body is in a steady state indicative of a fall for at least two seconds. This steady state will be substantially horizontal or greater than 45° in most cases. In this step, the angle α or the body angle data is monitored for at least two seconds.

If the lying condition has been met, the second step is examining the fall duration by looking at the data stored in a buffer. If the fall duration is below a time threshold, it is an uncontrolled fall. The fall duration is computed by examining the time event of the angle α or the body angle data.

The next step is determining the severity of the fall. Once an uncontrolled fall is detected, the rate of angular change of the body angle and acceleration amplitude change is used for determining the severity of the fall. A large rate of angular change and a large acceleration amplitude indicate a severe fall. The rate of angular body angle change and acceleration amplitude are compared to a severity threshold to determine whether a severe fall has taken place. The sensor system outputs four acceleration measures. Two of them are the X and Y axis acceleration measurements. The other two are Z-axis measurements. One measurement is in positive Z direction and the other is negative anti-parallel. After changing the sign of one of the negative Z-axis measurements, then the average of the two z-axis measurements is computed. The average is used as the final Z-axis measurement.

Figure 5:
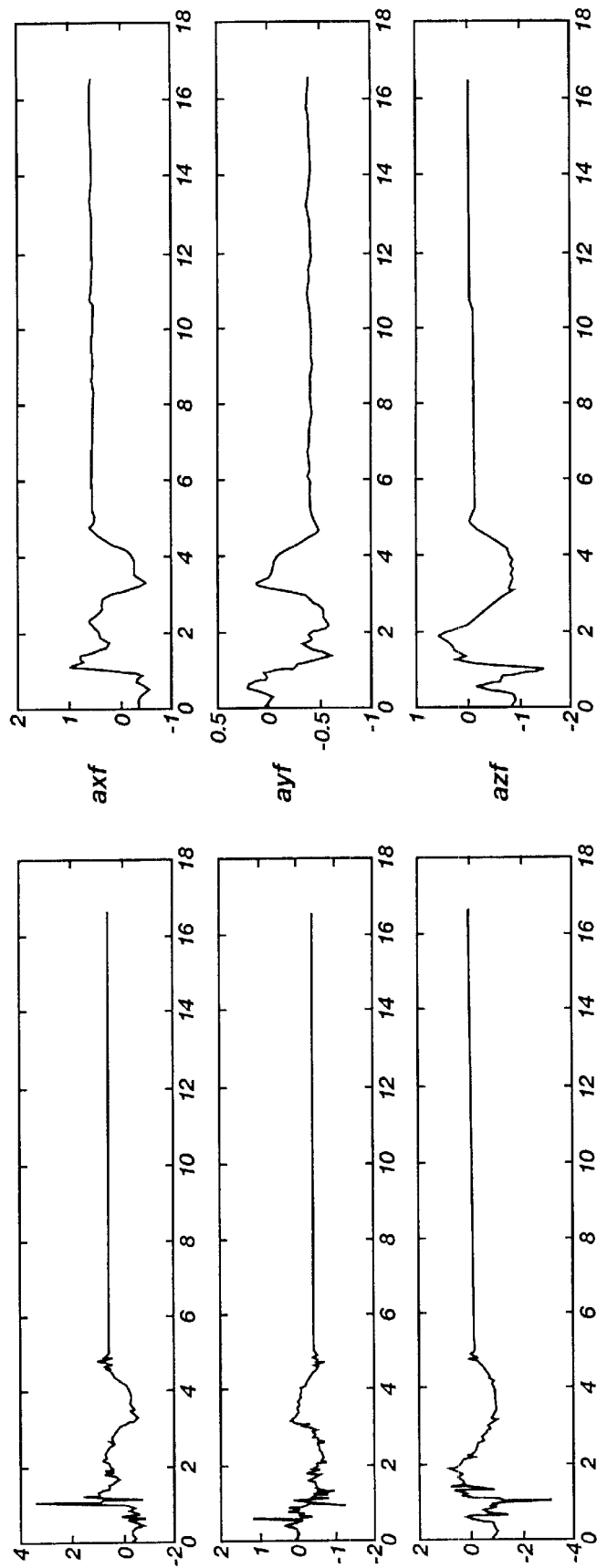
FIG. 5 illustrates raw and filtered fall acceleration data.
Figure 6:
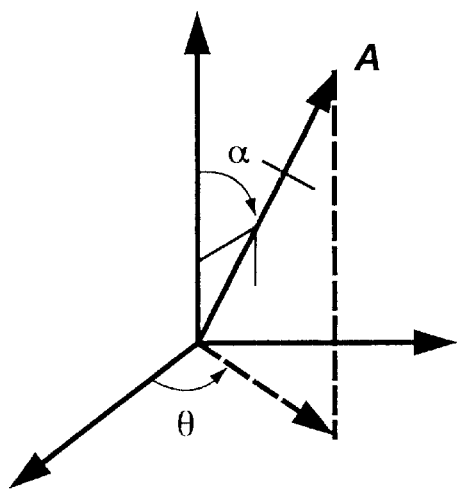
FIG. 6 illustrates a polar coordinate system.

The three axis acceleration measurements are filtered with a 5 Hz, second order Chebychev digital filter. This filtering can be done with analog circuitry in order to reduce the computational requirements. FIG. 5 depicts a comparison of the raw data and filtered data. For example, the raw data for the first displayed input line is ax and the filtered data for that input line is axf.

In this detection method, at least two seconds of data are collected. After performing the data preprocessing as described above, the mean of the acceleration for each axis is computed. The mean values of the three components of acceleration are used to compute the a and q used in the transformation matrices. After the calibration, the new acceleration is computed in the corrected coordinate system.

Figure 4:
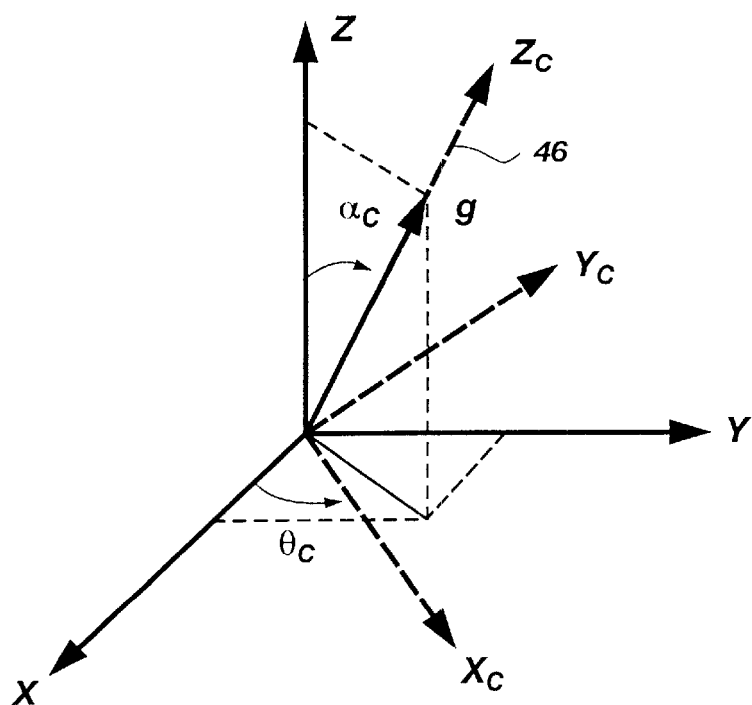
FIG. 4 represents the gravitational acceleration vector in a sensor coordinate system.

The angle α (FIG. 3 and FIG. 4) between the vertical axis and the body long axis plays an important role in fall detection. By converting the Cartesian representation into polar coordinates, the angle α is explicit. After the calibration is done, the system works with the data in the polar coordinate system.

After filtering, calibrating and representing the data in the polar coordinate system, the system is ready to detect if the user is in a substantially prone condition. Lying down (or a prone position) is defined as the user being in a horizontal orientation for at least two seconds. The system reads back through a 0.6 second window in time from the current sensor reading. If 75–80% of the data points in this window are greater than the threshold value (65°), this means that the user is lying down.

After detecting that the user is lying down, the system back traces through the fall data in the ring buffer to determine if a fall has occurred. The fall detection device should contain at least 4 seconds of buffered data or up to 10 seconds of data. The fall detection system assumes that an uncontrolled fall is a faster event than a controlled fall. The maximum and minimum angles are computed in a 0.2 second buffer window. If the difference between maximum and minimum acceleration exceeds a maximum body angle threshold, this means that an uncontrolled fall has occurred. Another valuable maximum body angle threshold is 50°, because if an individual body angle exceeds this angle α fall is likely to have occurred.

Figure 7:
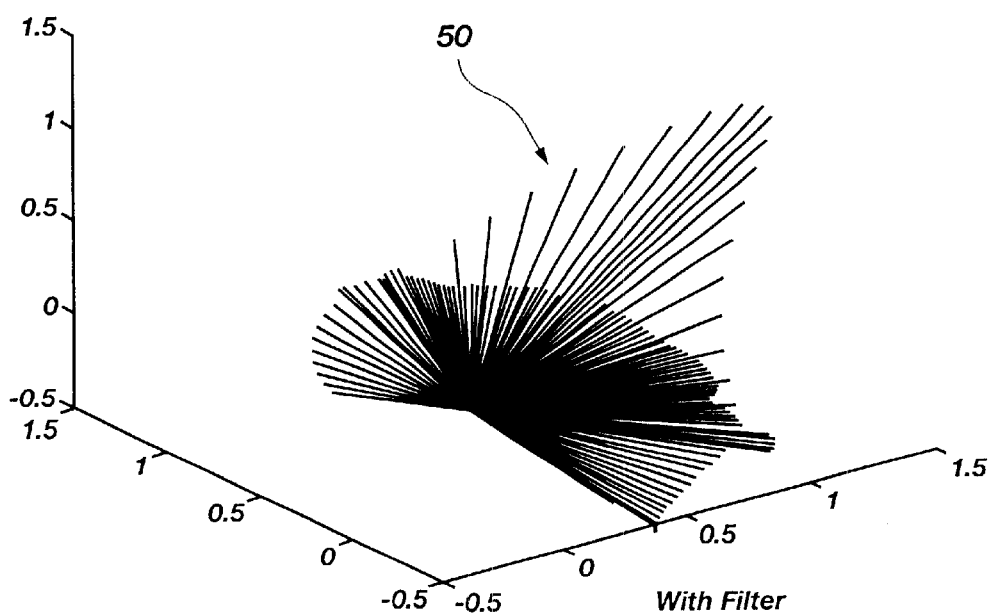
FIG. 7 represents acceleration data in a polar coordinate system.

Notice the large "α" angle change 50 due to the fall as depicted in FIG. 7. Each line in the figure represents a body position with respect to the vertical. The angle α represents body position, and length of the line represents magnitude of the acceleration vector.

Figure 8:
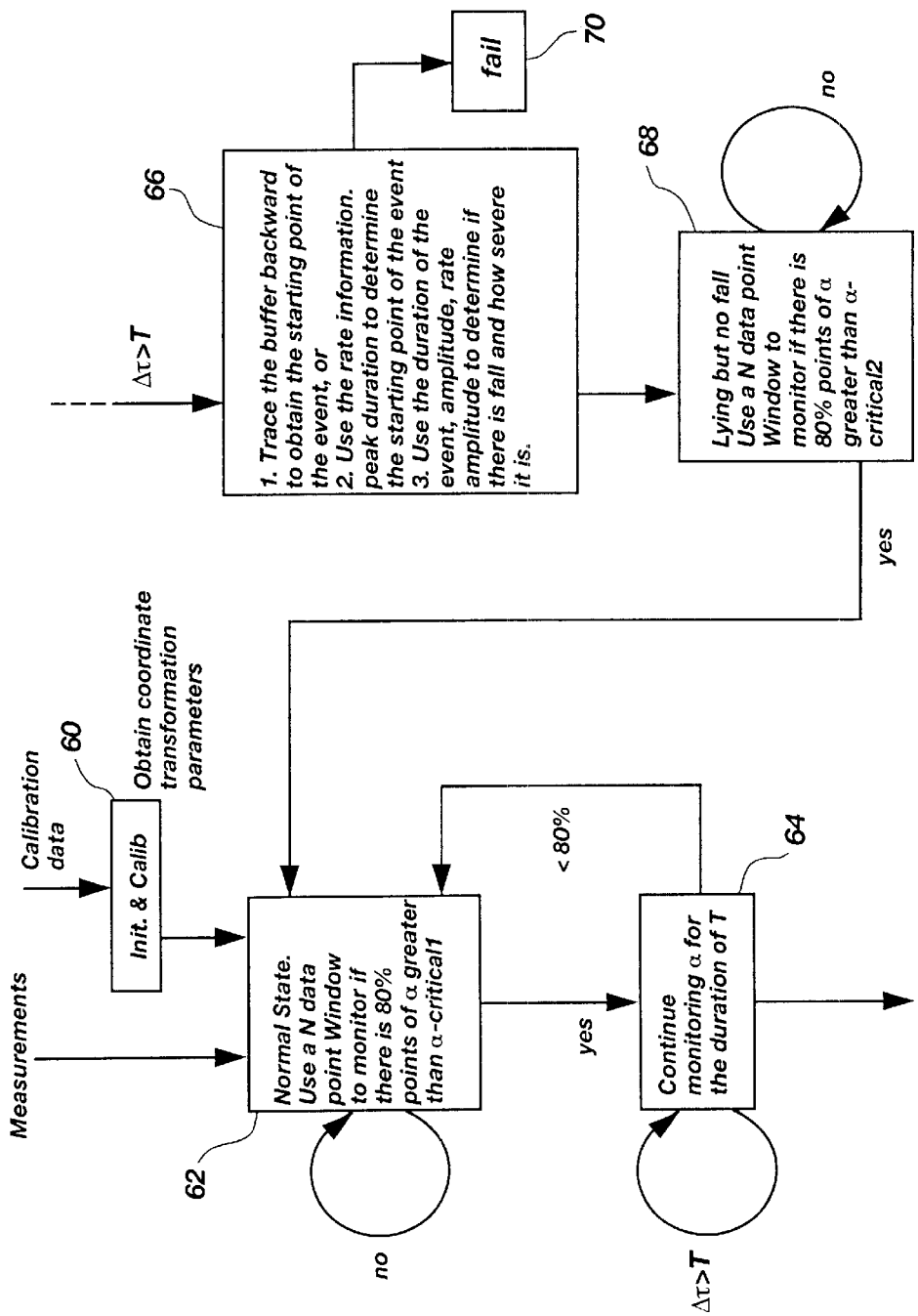
FIG. 8 is a flow diagram of the fall detection method.

FIG. 8 illustrates a flow chart of the method for detecting a fall. The first step includes the calibration of a gravity vector and a Cartesian coordinate transformation 60. Next the device begins to sample data and measure the "α" angle 62. The measurements are stored in a buffer which is configured to hold a certain number of data points (N). A predefined threshold is used to decide if enough data points are past a certain threshold angle. For example, the system will check to see if more than 75–80% of the data points are greater than a 50° angle from the calibrated gravity vector. Of course, the method can also use a threshold of 50% or more when checking the number of data points past a critical angle. Once it has been determined that there are a certain number of data points past a critical angle threshold and a fall is occurring, the system continues reading and storing angle data for a certain sampling time period T 64. The time T will preferably be a period of two seconds or more.

After the sampling time period has ended, the system traces backward in the buffer to obtain the starting point of the fall event 66. The rate of the fall and the peak duration are used to determine the starting point of the event. Then the event duration, event amplitude, and rate amplitude are used to determine if there is a fall and how severe the fall is 70. If the person is lying down but the data does not indicate a fall occurred, then the data window with N points is checked to determine if 75–80% of the data points are less than a critical value 68. If the criteria are met (no fall has occurred), the system returns to its original fall sampling mode. Otherwise, the system waits until these criteria are met before it returns to fall testing. This last step also allows any trailing fall data to be flushed from the buffer before fall testing begins again.

The overall accuracy of this method is almost 95% fall detection when using data obtained from waist mounted accelerometers. The fall detection system is also programmed to send a data signal to a receiver that interfaces to a telephone dialer.

Figure 9:
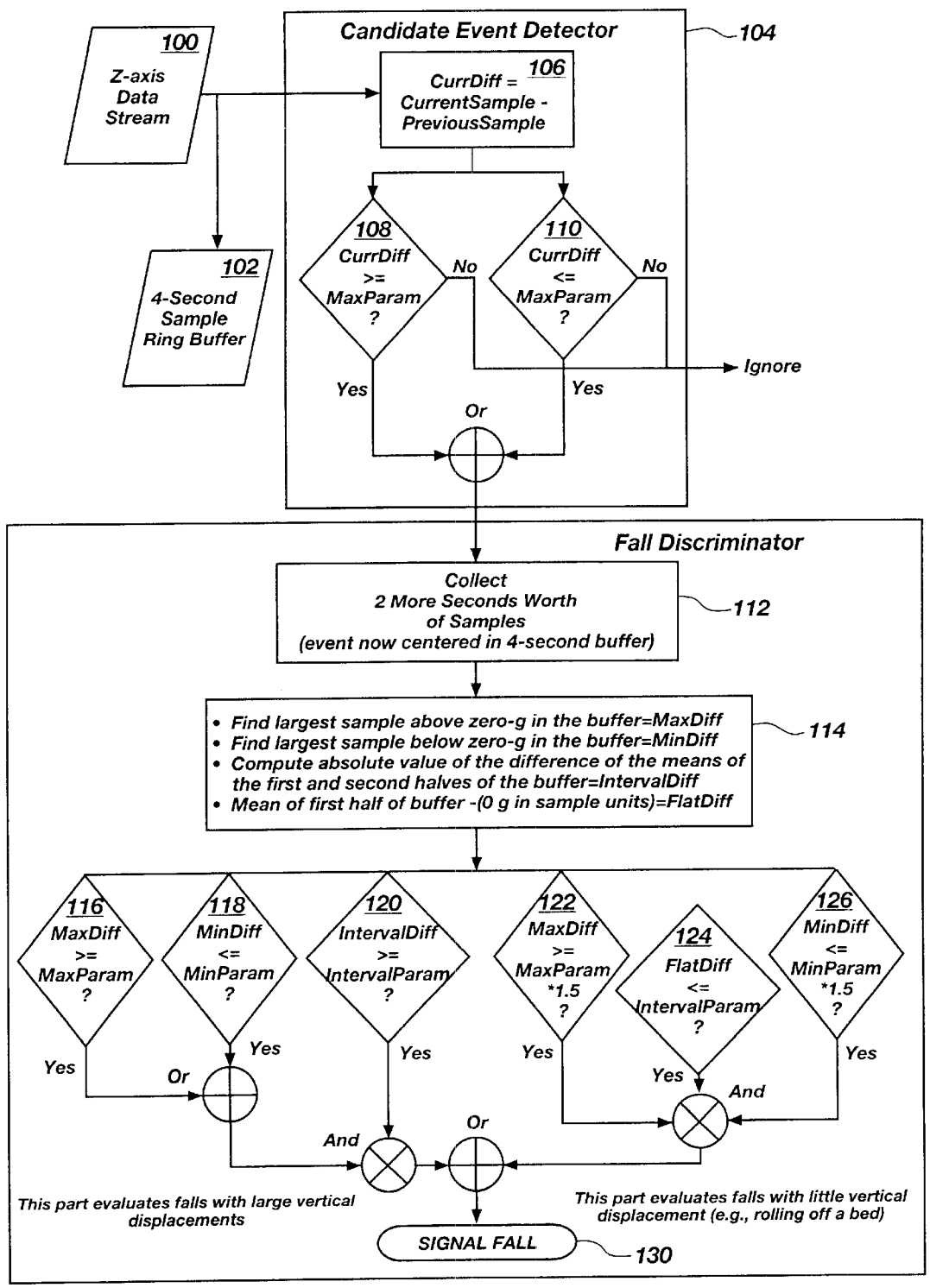
FIG. 9 is a flow diagram of the logic for another embodiment the fall detection method.

FIG. 9 illustrates an alternative embodiment of steps used to determine a fall. A simplification of the method discussed above avoids using a coordinate transformation and only uses the change in the Z axis acceleration. This avoids the complex coordinate transformation and allows the use of a less powerful and more affordable microcontroller with a short range radio link.

First a datastream is received from the Z-axis accelerometers 100 and this information is stored in a 4-second sample ring buffer 102. Of course, the buffer could be larger if desired. The candidate event detector decides if an event is taking place which could be the beginning of a fall. The event detector takes the difference in acceleration between the current sample and the previous sample 106. If the difference in acceleration between the two samples exceeds a maximum parameter (MaxParam) 108 or is less than a minimum parameter (MinParam) 110, then a potential fall event may be starting. When the sample differences do not exceed a certain maximum or minimum threshold, they are ignored.

If a fall has started, the steps in the fall discrimination portion of the algorithm are performed. Since a fall can be occurring, 2 more seconds of samples are collected 112. Next, the largest samples above and below zero gravity (zero-g) are found in the buffer 114. Then the absolute value of the difference of the mean of the first and second halves of the buffer are computed. The mean of the first half of the buffer is also stored for comparison purposes.

The fall discriminator then tests whether the fall includes a large vertical displacement. This is determined by comparing the largest sample above zero-g with a maximum acceleration threshold 116 or by comparing the smallest sample below zero-g with a minimum acceleration threshold 118. If either of these criteria is met, then a fall signal is produced. A vertical fall is also tested by comparing the absolute value of the mean of the first and second halves of the buffer with a maximum mean threshold 120. This measurement detects a large fall with a sustained acceleration that does not exceed a maximum or minimum threshold.

The fall discriminator also decides whether a fall has taken place with only a little vertical displacement. This is determined by comparing the largest sample above zero-g with 1.5 times the maximum acceleration threshold or by comparing the smallest sample below zero-g with 1.5 times the minimum acceleration threshold. If either of these criteria are met, then a fall signal is produced. A fall with little vertical displacement, such as rolling off a bed, is also tested by comparing the mean of the first half of the buffer with a predefined threshold or "flat" threshold. This measurement detects a rolling fall with sustained acceleration.

Although this invention does not directly prevent falls, the monitoring device does provide a number of advantages. For example, it enables the rapid arrival of help which decreases further damage caused by delayed intervention and medical care. The patient also receives a better prognosis for both short term medical aid and long term recovery due to the faster arrival of help. A historical recording of the fall event aids in determining the problem severity and what action should be taken by caregivers. These advantages lead in turn to the patient having greater confidence to live independently. Increased safety at a low cost is also provided because a patient can live without continuous companionship and/or assistance.

In nursing homes where a monitoring station is installed, the system facilitates diagnosis by providing a history of a patient's body motion and position directly preceding, during, and after a fall. The result is improved patient care in nursing home facilities with smaller numbers of nursing personnel. In the case of elderly patients living independently in homes, they receive increased safety and extended length of independent quality life.

Other advantages are provided for nursing home personnel. The nursing home can monitor the actual physical status of all their patients without individual observation. Then if a fall or some similar accident occurs, the nursing home will immediately know the severity of the fall and the current body position of the patient. Information about the fall and the body position of the patient during and after the fall is recorded to provide a history for the patient.

There are also advantages produced for the patient's relatives and other part time careproviders. Relatives who are caring for the patient or elderly person who has the present device will be able to work outside the home without the need for hiring permanent, live-in help. The automatic sensors and monitoring of this invention also allow relatives and careproviders to have increased confidence that in case of an emergency the fall monitor will provide instant notification. Professional careproviders also benefit from the fall monitor because there in an improved ability to organize help quickly with a minimum of interruption to their other professional activities. This is because the device can detect the severity of the accident and then the appropriate emergency care may be sent without the careprovider providing further analysis.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims.

What is claimed is:

1. A method for monitoring a person's fall using an accelerometer included in a personal monitoring device configured to be carried on the person, having a microprocessor and a memory buffer, wherein data is stored in the buffer of the personal monitoring device, comprising the steps of:
   (a) sampling an output from the accelerometer indicative of body acceleration and body angle;
   (b) detecting whether the body angle is in a steady state indicative of a fall for at least two seconds;
   (c) measuring a fall duration by reading back through the buffer;
   (d) determining if an uncontrolled fall has taken place by testing whether the fall duration is less than a time threshold; and
   (e) determining whether a severe fall has occurred by comparing an angular rate of change of the body angle and an acceleration amplitude change to a severity threshold.

2. A method as in claim 1, further comprising the step of signaling a fall via a communications network when a severe fall has taken place.

3. A method as in claim 1, further comprising the step of calculating the severity of an uncontrolled fall by comparing angular rate of change and an amplitude change to a severity threshold.

4. A method as in claim 1, wherein the step of measuring the fall duration further comprises using time duration data for measuring the fall duration using body angle data stored in the buffer.

5. A method as in claim 1, further comprising the step of determining whether the fall duration is less then a time threshold of approximately 0.335 seconds, which indicates that the person's fall is an uncontrolled fall.

6. A method as in claim 1, wherein the step of determining body angle further comprises the step of determining body angle using an output from a three-dimensional accelerometer.

7. A method as in claim 6, further comprising the step of determining the body angle using an output from a three-dimensional accelerometer that is filtered with a Chebychev filter.

8. A method as in claim 1, further comprising the step of storing fall data in a ring buffer.

9. A method as in claim 1, further comprising the steps of providing a sensor coordinate system and transforming the sensor coordinate system by rotating the sensor coordinate system to align a gravity vector with a Z-axis.

10. A method as in claim 9, further comprising the step of creating a transformed Y-axis of the coordinate system which is perpendicular to the Z-axis of the transformed sensor coordinate system.

11. A method as in claim 9, further comprising creating a transformed X-axis of the sensor coordinate system that is determined by a right-hand rule based on the Y and Z axes of the transformed coordinate system.

12. A method for monitoring a person's fall using an accelerometer in a monitoring device carried on the person, which monitoring device samples the person's body angle and body acceleration, comprising the steps of:
   (a) providing a buffer in the monitoring device and storing body angle and body acceleration data therein;
   (b) detecting whether the body angle is in a horizontal steady state for at least two seconds;
   (c) measuring a fall duration using time duration data for the person's body angle stored in the buffer of the monitoring device;
   (d) determining whether the fall duration is less then a time threshold indicating that the fall is an uncontrolled fall; and
   (e) determining the severity of the uncontrolled fall using an angular rate of change of the body angle and an acceleration amplitude change.

13. A method as in claim 12, further comprising the step of repeating steps (a)–(d) until an uncontrolled fall is detected.

14. A method as in claim 12, further comprising the step of using a Cartesian coordinate system with the accelerometer to detect the rate of change of the body angle.

15. A method as in claim 14, further comprising the step of converting the Cartesian coordinate system to a polar coordinate system in order to perform explicit angle calculations.

16. A method as in claim 12, further comprising the step of storing fall data in a ring buffer.

17. A method as in claim 16, wherein the step of detecting whether the body angle is in a horizontal steady state for at least two seconds, further comprises the step of reading back at least one-half second in the ring buffer to decide if the person is in a horizontal position.

18. A method as in claim 17, further comprising the step of comparing body angle data stored in the buffer to a threshold value to determine if a person is in a horizontal position, wherein the threshold comprises that at least 50% of body angle data in the buffer is greater than 50°.

19. A method as in claim 17, step of comparing body angle data stored in the buffer to a threshold value to determine if a person is in a horizontal position, wherein the threshold comprises that at least 80% of body angle data in the buffer is greater than 50°.

20. A method as in claim 16, further comprising the step of storing at least 4 seconds of fall data in the ring buffer.

21. A method as in claim 16, further comprising the step of comparing maximum body angles, in a 0.2 second window of the ring buffer, to a maximum body angle threshold.

22. A method for monitoring a person's fall using a single-dimensional accelerometer in a personal monitoring device, comprising the steps of:
   (a) detecting whether an acceleration exceeds a trigger threshold;
   (b) collecting at least 2 seconds of additional acceleration data in a buffer after the acceleration exceeds a trigger threshold; and
   (c) finding a largest acceleration sample value in the buffer; and
   (d) signaling that a fall has taken place when the largest acceleration sample value exceeds a maximum threshold.

23. A method as in claim 22, further comprising the step of detecting whether a mean acceleration within a buffer window exceeds a maximum mean threshold.

* * * * *

UNITED STATES PATENT AND TRADEMARK OFFICE
CERTIFICATE OF CORRECTION

PATENT NO. : 6,433,690 B2
DATED : August 13, 2002
INVENTOR(S) : Stephen C. Jacobsen It is certified that error appears in the above-identified patent and that said Letters Patent is hereby corrected as shown below:

Title page,
Item [75], Inventors, replace "Steven C. Jacobsen" with -- Stephen C. Jacobsen --, Column 2,
Line 48, before "the" insert -- of --, Column 3,
Line 54, after "(e.g., a eather belt)" delete "and", Column 4,
Line 29, after "In the event of" insert -- a --, Column 5,
Lines 6, 8, 11, 15 and 22, replace "z-axis" with -- Z-axis --,
Line 14, "in the upright position" delete "and", Column 6,
Line 14, replace "z-axis" with -- Z-axis --,
Line 56, replace "α" with -- a --, Column 8,
Line 54, replace "in" with -- is --.

Signed and Sealed this

Twenty-fourth Day of August, 2004

JON W. DUDAS
*Director of the United States Patent and Trademark Office*